United States Patent [19]

Humber et al.

[11] Patent Number: 5,958,445
[45] Date of Patent: Sep. 28, 1999

[54] ORAL FORMULATIONS OF S(+)-ETODOLAC

[75] Inventors: Leslie G. Humber, Brunswick, N.J.; Gerald L. Reuter, Plattsburgh, N.Y.

[73] Assignee: American Home Products Corporation, Madison, N.J.

[21] Appl. No.: 09/006,980

[22] Filed: Jan. 14, 1998

Related U.S. Application Data

[63] Continuation-in-part of application No. 08/661,269, Jun. 10, 1996, abandoned.
[60] Provisional application No. 60/000,171, Jun. 13, 1995.
[51] Int. Cl.$^6$ .................. A61K 9/10; A61K 9/14; A61K 9/20; A61K 9/46
[52] U.S. Cl. ............ 424/439; 424/440; 424/441; 424/442; 424/464; 424/465; 424/466; 424/489; 514/784; 514/937; 514/970; 514/974
[58] Field of Search ............... 424/489, 441, 424/464, 465, 466, 440, 438, 442, 439; 514/784, 937, 970, 974

[56] References Cited

U.S. PATENT DOCUMENTS

| | | | |
|---|---|---|---|
| 2,260,148 | 10/1941 | Mable | 426/3 |
| 3,228,831 | 1/1966 | Nicholson et al. | 514/568 |
| 3,939,178 | 2/1976 | Demerson | 548/432 |
| 4,265,847 | 5/1981 | Hunt et al. | 264/122 |
| 4,305,502 | 12/1981 | Gregory et al. | 206/532 |
| 4,371,516 | 2/1983 | Gregory et al. | 424/485 |
| 4,520,203 | 5/1985 | Abraham et al. | 548/432 |
| 4,639,368 | 1/1987 | Niazi et al. | 424/48 |
| 4,764,378 | 8/1988 | Keith et al. | 424/435 |
| 4,788,220 | 11/1988 | Mody et al. | 514/557 |
| 4,800,087 | 1/1989 | Mehta | 424/497 |
| 4,835,186 | 5/1989 | Reuter et al. | 514/570 |
| 4,835,187 | 5/1989 | Reuter et al. | 514/570 |
| 4,835,188 | 5/1989 | Reuter et al. | 514/570 |
| 4,851,226 | 7/1989 | Julian et al. | 424/441 |
| 4,851,444 | 7/1989 | Sunshine et al. | 514/570 |
| 4,861,797 | 8/1989 | Haas | 514/557 |
| 4,877,620 | 10/1989 | Loew et al. | 424/451 |
| 4,879,108 | 11/1989 | Yang et al. | 424/440 |
| 4,942,039 | 7/1990 | Duvall et al. | 424/466 |
| 4,966,768 | 10/1990 | Michelucci et al. | 424/468 |
| 5,084,278 | 1/1992 | Mehta | 424/441 |
| 5,190,981 | 3/1993 | Wechter | 424/49 |
| 5,225,197 | 7/1993 | Bolt et al. | 424/440 |
| 5,380,535 | 1/1995 | Geyer et al. | 424/484 |
| 5,458,879 | 10/1995 | Singh et al. | 424/400 |

FOREIGN PATENT DOCUMENTS 9317680  9/1993  WIPO.

OTHER PUBLICATIONS

Translation of Seractil 200 mg package insert (1983).
J. Med. Chem., vol. 26, No. 12, 1778–1780 (1983).

*Primary Examiner*—Thurman K. Page
*Assistant Examiner*—James M. Spear
*Attorney, Agent, or Firm*—Steven R. Eck

[57] ABSTRACT

This invention discloses organoleptically acceptable formulations containing non-solubilized S(+) 1,8-diethyl-1,3,4,9-tetrahydropyrano[3,4-b]indole-1-acetic acid, preferably with an acidic component, also known as S(+)etodolic acid or S(+)etodolac.

12 Claims, No Drawings

ORAL FORMULATIONS OF S(+)-ETODOLAC

This application is a continuation-in-part of U.S. application Ser. No. 08/661,269, filed Jun. 10, 1996, abandoned which claims priority from U.S. Provisional Application No. 60/000,171. filed Jun. 13, 1995.

This invention relates to novel formulations of etodolac, also known as etodolac acid. More particularly, this invention relates to organoleptically acceptable oral formulations utilizing S(+)-etodolac. For the purposes of this description, organoleptically acceptable compounds, materials and formulations are those which can contact the taste receptors of the recipients mouth, particularly those in which the active ingredient can contact the taste receptors, and which are generally acceptable to the senses of the recipient, particularly the sense of taste. More particularly, the organoleptically acceptable formulations of this invention are those in which the S(+)-etodolac component does not have the unpleasant, bitter taste normally associated with a racemic mixture of etodolac or of S(+)-etodolac in solution.

BACKGROUND OF THE INVENTION

Etodolac is a nonsteroidal antiinflamatory drug (NSAID) that exhibits anti-inflammatory, analgesic, and antipyretic activities in animal models. Like that of other NSAIDs, the mechanism of etodolac is not completely understood, but is believed to be associated with an inhibition of prostaglandin biosynthesis. Etodolac is presently marketed by Wyeth-Ayerst Laboratories in the form of Lodine® tablets and capsules, which utilize a racemic mixture of etodolac.

U.S. Pat. No. 3,939,178 (Demerson et al.) teaches and claims certain pyrano[3,4-B]indoles and thiopyrano[3,4-B] indoles which include the (±) 1,8-diethyl-1,3,4,9-tetrahydropyrano[3,4-B]indole-1-acetic acid ingredient of Lodine® tablets and capsules.

The Physicians' Desk Reference, 49 Edition, 1995, at page 2682, teaches that etodolac is insoluble in water but soluble in alcohols, chloroform, dimethyl sulfoxide and aqueous polyethylene glycol.

U.S. Pat. No. 4,710,511 (Wooley) discloses a method of using etodolac compositions for inhibiting joint ankylosis for the treatment of arthritides. U.S. Pat. No. 4,742,076 teaches a method of using such compounds for lowering rheumatoid factor blood level. U.S. Pat. No. 4,966,768 (Michelucci et al.) describes a sustained release form of etodolac having as essential components etodolac, hydroxypropylmethylcellulose, ethylcellulose and a release rate modifying agent such as dibasic sodium phosphate, the hydroxypropylmethylcellulose having a hydroxypropoxyl content of about 7.0% to 8.6% by weight.

Demerson et al. disclose in the Journal of Medicinal Chemistry, 1983, Vol. 26, No 12, pp. 1778–1780, that biochemical and pharmacological tests showed that virtually all of the effects of etodolac are due to the S(+) enantiomer.

PCT application WO 93/17680 teaches methods and compositions utilizing optically pure R(−) etodolac for the treatment of pain. WO 93/17680 indicates that the optically pure R(−) etodolac substantially reduces certain purported adverse effects associated with the administration of the racemic mixture of etodolac.

Because of its unpleasant, bitter taste, etodolac has not, without some form of coating or taste-masking, been fully utilized in many formulations which would allow the etodolac to contact the recipient's taste buds. It is, therefore, significant that this invention provides organoleptically acceptable formulations containing uncoated and unmasked etodolac as an active ingredient. It is also significant that the production of the formulations of this invention do not require the additional formulation steps of coating the etodolac ingredient or incorporating taste masking ingredients into the formulations.

DESCRIPTION OF THE INVENTION

Etodolac is a pyranocarboxylic acid chemically designated as (±) 1,8-diethyl-1,3,4,9-tetrahydropyrano[3,4-b] indole-1-acetic acid, also known as etodolic acid, which has the structural formula:

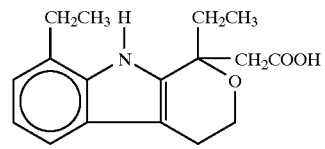

and is currently marketed as a racemic mixture in Lodine® etodolac tablets and capsules by Wyeth-Ayerst Laboratories, Division of American Home Products Corporation, P.O. Box 8299, Philadelphia, Pa. 19101. Etodolac is a non-steroidal anti-inflammatory drug (NSAID) that exhibits anti-inflammatory, analgesic and antipyretic activities, which are well documented in the art. Etodolac can be prepared by methods known in the art, such as those described in U.S. Pat. No. 3,939,178 (Demerson et al.), which is incorporated herein by reference. The racemates of etodolac may also be resolved by methods known in the art. For instance, they may be resolved by the crystallization of diastereomeric salts with (+)-cinchonine to afford (+)-etodolac of approximately 100% enantiomeric purity in an overall yield of 81%, with recovery of the (+)-cinchonine, as described in U.S. Pat. No. 4,520,203 (Abraham et al.).

It has been discovered that the dextrarotatory or S(+) form of etodolac, S(+) 1,8-diethyl-1,3,4,9-tetrahydropyrano[3,4-b]indole-1-acetic acid, which may also be referred to herein as the eutomer of etodolac or the etodolac eutomer, does not contain the unpleasant, bitter taste of the racemic etodolac if it is not solubilized. It is, therefore, now understood and considered as within the scope of this invention that the use of the undissolved S(+) stereoisomer of etodolac substantially free of its R(−) form, preferably free of its R(−) form, enables one to create a wide variety of etodolac formulations which are pharmaceutically and organoleptically acceptable for oral administration.

Not only does this knowledge provide those skilled in the art the ability to create organoleptically acceptable etodolac formulations, it does so without the need for the additional steps of coating or taste masking the etodolac. In many cases, the technique for coating pharmaceutical materials is imperfect, leaving a portion of the compound in question accessible to the taste buds. Likewise, in formulations where chewing is likely to occur, the grinding action of the teeth can puncture coated particles in the formulation to release some of the unpleasant tasting material. By starting with an acceptable tasting base ingredient, the formulations of this invention eliminate the chance of an unexpected release of unpleasant materials. This improvement not only improves the marketability and reduces production costs of such formulations, it can also improve the recipient's compliance with a prescribed dosage regimen.

In view of this knowledge, the present invention comprises organoleptically acceptable oral formulations comprising, alone or in conjunction with other organoleptically and pharmaceutically acceptable components, the S(+) stereoisomer of etodolac substantially free of its R(−) form, preferably free of its R(−) form. These oral formulations include those orally administerable formulations in which active ingredients and other components of the formulation may normally be presented to the taste and or smell receptors of the recipient. Such formulations include those which do not solubilize the S(+)-etodolac, but are not limited to, organoleptically acceptable etodolac liquid dispersions, suspensions, emulsions, syrups, colloids, sachets, tablets, including chewable, buccal and sublingual tablets, powders or granular compositions, effervescent formulations, cachets, troches or lozenges, pastes, foams, dentifrices and gels. Because of the use of NSAIDs in veterinary medicine, formulations which are organoleptically acceptable to animals, particularly companion animals such as cats and dogs, can be produced within the scope of this invention.

In its simplest form, this invention comprises an organoleptically acceptable etodolac formulation which comprises the etodolac eutomer, alone. This compound may be taken alone for the relief described in the art for etodolac. The eutomer of etodolac may also be taken with water, fruit juices, soft drinks, milk or other liquids or beverages being used to assist in the oral administration of the drug. Other simplified administrations can include the administration of the eutomer to food, which may then be consumed in the normal fashion. These food-related or drink-related routes of administration may be preferred by any number of recipients, particularly children.

It is preferred that the formulations of this invention containing the etodolac eutomer also contain an acidic component of sufficient amount to maintain the pH of the formulation below 7, preferably between 2 and 6. Pharmaceutically acceptable acids for use in these formulations include, but are not limited to, commonly used food acids such as citric acid, tartaric acid, malic acid, fumaric acid, lactic acid, adipic acid, ascorbic acid, aspartic acid, erythorbic acid, glutamic acid, and succinic acid.

The formulations of the present invention may be considered those comprising a pharmaceutically effective amount of non-solubilized S(+)-etodolac and an acidic component, preferably a food acid, the acidic component being present in sufficient amount to maintain the pH of the formulation below 7, preferably between 2 and 6, more preferably between about 2 and about 5.

The present formulations include those in which the S(+)-etodolac is not solubilized, i.e. the acid form of (+) 1,8-diethyl-1,3,4,9-tetrahydropyrano[3,4-b]indole-1-acetic acid in the absence of any material in which the acid is reasonably soluble. Common pharmaceutically useful components in which the acid is soluble include alcohols, dimethyl sulfoxide (generally used for topical applications), propylene glycol and aqueous polyethylene glycols. The salt forms of (+) 1,8-diethyl-1,3,4,9-tetrahydropyrano[3,4-b] indole-1-acetic acid are also soluble in water and, depending upon their degree of solubility, may impart a bitter taste to an orally administered formulation.

The etodolac eutomer-containing compositions of this invention may be used in the manner and for the dosages suggested for the Lodine® tablets and capsules presently on the market. It will be understood by those skilled in the art that etodolac, like other NSAIDs, may exhibit a variation in response from individual to individual. Therefore, the recommended initial therapeutic dose should be one which is likely to be effective for the majority of recipients, with the dosage being adjusted thereafter according to the beneficial and adverse effects observed by the recipient.

Etodolac administration in healthy, young to middle-aged adults has shown symptom relief for acute pain lasting 5 to 6 hours following single etodolac doses of 400 mg and relief lasting 4 to 5 hours following 200 mg doses. Formulations of this invention include dosage of the etodolac eutomer from as low as 10 mg or lower to as high as 1,000 mg or more. A recommended etodolac dosage for the formulations of this invention would be an initial 200–400 mg dose, followed every 6 to 8 hours by doses of 50 mg to 400 mg, preferably 200 mg to 400 mg. For relief of the symptoms of osteoarthritis, a starting dose of 800 to 1200 mg/day in divided doses may be required. These divided doses may be 400 mg t.i.d. or b.i.d. or 300 mg q.i.d. or t.i.d. As with other NSAIDs, the lowest dose and longest dosing interval which alleviates symptoms is recommended. The recommended total daily dose of etodolac using the compositions described and claimed herein is 600 to 1200 mg/day given in divided doses, such as 400 mg t.i.d. or b.i.d., 300 mg q.i.d., t.i.d. or b.i.d., or 200 mg q.i.d. or t.i.d. It will be understood that, despite the amount of etodolac eutomer listed in the examples that follow, the formulations below may be created with any dose of the etodolac eutomer described above.

While the etodolac eutomer of this invention does not impart an undesirable taste to formulations in which it is used, the formulations described herein may include sweetening or flavoring agents to increase the overall flavor, taste and desirability of the formulation. Such sweetening agents may include all pharmaceutically acceptable sweetening agents including, but not limited to, molasses, glycine, corn syrup, sugars, such as sucrose, glucose, fructose and confectioner's sugar, sorbitol, saccharin, saccharose, saccharin sodium, saccharin calcium, aspartame (available under the Nutrasweet® trademark, Nutrasweet Company, Deerfield, Ill.), stevioiside, neohesperidyl dihydrochalcone, glycyrrhiza, perillaldehyde, xylitol, dextrose, mannitol and lactose.

The formulations herein may also include pharmaceutically acceptable excipients, fillers, diluents, lubricants, disintegrants, suspending or stabilizing agents, and binding agents including, but not limited to, aluminum stearate, magnesium stearate, sodium lauryl sulfate, microcrystalline cellulose, polyvinylpyrrolidone, gelatin, alginic acid, acacia gum, sodium citrate, complex silicates, calcium carbonate, glycine, dextrin, sucrose, sorbitol, dicalcium phosphate, calcium sulfate, lactose, kaolin, mannitol, sodium chloride, talc, dry starch (e.g. corn, potato or tapioca starch) and powdered sugar.

In a simple form, the formulations of this invention would include powdered or granular dosage formulations containing the etodolac eutomer. For instance, the eutomer can be taken orally, by itself, in a powdered or granular form. The recipient may wish to place such a powdered or granular formulation into his mouth and wash it down by drinking a liquid or eating a solid food. Because of the relatively small volume of S(+) etodolac found in the dosages described herein, it may be preferable to include in the powdered or granular dosage form one or more organoleptically acceptable powdered pharmaceutical components. These may be compounds with additional pharmaceutical activities or fillers, sweeteners, etc. as described herein. It will be understood that any dosage of etodolac eutomer can be administered in this way, with the volume of additional components being limited only to the amount found acceptable to a recipient. In the case of such solid formulations of this invention it is understood that the indicated pH is imparted upon the acidic components contact with liquid, such as the recipient's saliva.

With the use of this S(+) eutomer of etodolac, organoleptically acceptable oral liquid etodolac dosage forms can be formulated and utilized. Such liquid formulations may be created with a water base.

These oral liquids may include any oral liquid formulations utilizing the eutomer of etodolac, including the mere incorporation of the desired dose of etodolac eutomer into a normally consumed amount of beverages and drinks including for example, but not limited to, carbonated or non-carbonated water, fruit juices, coffee, tea, soft drinks and milk. Because of the relatively small volume occupied by a single dose of the etodolac eutomer, it may be preferable to incorporate the eutomer into a small, manageable amount of one or more pharmaceutically elegant and organoleptically acceptable materials, such as those described herein.

In one type of preferred oral liquid of this invention, the oral liquid comprises from about 0.8% to about 4% etodolac eutomer weight by volume of the total composition, about 0.1% to about 2% weight by volume of the total composition of suspension stabilizing agents, about 20% to about 70% by weight of the total composition of one or more flavoring agents, about 30% to about 70% weight by volume of the total composition of water, with the composition containing a pharmaceutically and organoleptically acceptable food acid, such as citric acid or phosphoric acid, in an amount of 0.1% to about 2% weight by volume. Preferably the suspending agents include xanthan gum, microcrystalline cellulose, sodium carboxymethylcellulose and polysorbate 80. Examples 1 and 2, below, describe how two such formulations may be produced.

EXAMPLE 1

| Ingredient | Percent Wt/Vol. | Grams Per 15 Liters |
|---|---|---|
| Xanthan Gum | 0.15 | 22.5 |
| Microcrystalline Cellulose | 0.75 | 112.5 |
| Sodium Benzoate, NF | 0.25 | 37.5 |
| Citric Acid, Monohydrate, USP | 0.95 | 142.5 |
| Sucrose, NF | 50.00 | 7500.0 |
| Corn Syrup | 20.00 | 3000.00 |
| Etodolac, Eutomer | 2.0 | 300.0 |
| Sodium Carboxymethylcellulose, USP | 0.10 | 15.0 |
| Polysorbate 80, NF | 0.30 | 45.0 |
| Red FDC 40 Color | 0.15 | 2.25 |
| Disodium Edetate, USP | 0.05 | 7.5 |
| Artificial Lime Flavor Oil | 0.16 | 24.0 |
| Phosphoric Acid | q.s. to pH 3.0–3.5 | q.s. to pH 3.0–3.5 |
| Purified Water, USP | q.s. to 100 mL | q.s. to 15000 mL |

A first portion of this oral liquid formulation may be prepared by first placing the corn syrup into a jacketed kettle equipped with a stirrer. Then the sodium carboxymethyl cellulose component is sprinkled onto the solution and mixed for 10 minutes until it becomes completely wet. The mixture should then be heated to about 70° C. and mixed until the gum is completely hydrated, followed by cooling of the mixture to 45° C. and addition of the polysorbate 80 component. Mixing is continued while cooling the mixture to 30° C. The etodolac, eutomer is sprinkled slowly into the mixture and mixing continued for 15 minutes.

A second portion is then created by placing the required amount of water into a container equipped with a propeller-type mixer and adding slowly and hydrating the xanthan gum by mixing with a high shear for approximately 25 minutes. This should be followed by placing into a separate mixing vessel, equipped with a propeller type mixer, a quantity of water equivalent to about 30% to 40% by volume of the total batch (4500 to 6000 mL). The microcrystalline cellulose may then be sprinkled onto the water and mixed at medium shear for about 30 minutes to completely disperse the cellulose.

The required amount of the xanthan gum solution from the first portion, above, is added to the cellulose suspension with mixing for about 15 minutes or until a uniform suspension is obtained. This is followed by slow addition of the sucrose with mixing for about 15 minutes, or until no sucrose particles are observed. Coloring agents, such as the Red FDC 40 Color mentioned above, may be added and mixed until dispersed throughout the mixture.

This is followed by addition of the slurry from the first portion, above, and slowly mixing for about 15 minutes. The sodium benzoate, disodium edetate and citric acid and flavoring are then added and mixed for about 5 minutes after each addition. The phosphoric acid component is added with mixing until the formulation reaches a pH from about 3.0 to about 3.5. The final formulation should be balanced with water and mixed until the formulation is homogenous.

EXAMPLE 2

Another example of an oral liquid formulation utilizing S(+) 1,8-diethyl-1,3,4,9-tetrahydropyrano[3,4-b]indole-1-acetic acid, the eutomer of etodolac, is the following:

| Ingredient | Percent Wght/Vol. | Grams Per 15 Liters |
|---|---|---|
| Xanthan Gum | 0.15 | 22.5 |
| Microcrystalline Cellulose | 0.75 | 112.5 |
| Sodium Benzoate, NF | 0.25 | 37.5 |
| Citric Acid Hydrous, USP | 0.95 | 142.5 |
| Sucrose, NF | 50.00 | 7500.0 |
| Maltitol Syrup | 20.0 | 3,000.00 |
| Etodolac Eutomer | 2.0 | 300.0 |
| Sodium Carboxymethylcellulose, USP | 0.10 | 15.0 |
| Polysorbate 80, NF | 0.30 | 45.0 |
| Red FDC 40 Color | 0.015 | 2.25 |
| Disodium Edetate, USP | 0.05 | 7.5 |
| Artificial Lemon Flavor Oil | 0.16 | 24.0 |
| Hydrochloric Acid | q.s. to pH 2.5–3.5 | q.s. to pH 2.5–3.5 |
| Purified Water, USP | q.s. to 100 mL | q.s. to 15000 mL |

This preparation may be prepared by measuring the maltitol syrup into a jacketed kettle equipped with a stirrer. Into this solution is sprinkled the sodium carboxymethylcellulose, which is mixed for 10 minutes or until all of the particles are completely wet. The resulting mixture is then heated to about 70° C. and mixed until the gum is completely hydrated, after which the mixture is cooled to 45° C. and the Polysorbate 80 is added. Mixing is then continued while the mixture is cooled to 30° C. The etodolac eutomer is then added slowly into the mixture and mixing is continued for 15 minutes to produce what is referred to below as the etodolac slurry.

A second solution, which may be referred to as the xanthan gum solution, is prepared first in the form of a 1% by weight xanthan gum solution in water. The xanthan gum should be added slowly to the water and mixed at high shear for approximately 25 minutes. Into a separate mixing vessel equipped with a mixer is placed a volume of water equivalent to 30% to 40% weight by volume of the total batch (4500 to 6000 mil). The microcrystalline cellulose is then sprinkled onto the water and mixed at medium shear for 30 minutes or until the microcrystalline cellulose is completely suspended. The required amount of xanthan gum solution is then added to the microcrystalline cellulose suspension with mixing for 15 minutes or until a uniform suspension is obtained.

The sucrose is then added slowly to the second solution with mixing for 15 minutes or until no sucrose particles are observed. The coloring agents may then be added. The required amount of the etodolac slurry is then added slowly and mixed for 15 minutes. The sodium benzoate, disodium edetate and citric acid are then sequentially added and mixed for 5 minutes following each addition. The hydrochloric acid component is added with mixing until the formulation reaches a pH from about 2.5 to about 3.5. The remainder of the water is then added with mixing until the formulation is homogenous.

EXAMPLE 3
Chewable Tablets Containing the Etodolac Eutomer

Chewable tablets containing the etodolac eutomer and falling within the scope of this invention will be understood to include those chewable tablet formulations known in the art to be pharmaceutically and organoleptically acceptable. These formulations will include those having a) etodolac eutomer in the dosage amounts described herein; b) from about 5 mg to about 400 mg, preferably from about 10 mg to about 200 mg, of a solid acidifier component, such as the food acid components described herein; and c) from about 50 mg to about 5 g, preferably from about 100 mg to about 1 g, of a pharmaceutically and organoleptically acceptable excipient, such as dextrates, maltodextrins, lactose, modified food starches, aluminum stearate, chewing gum base, and compactable food grade sugars, as well as other materials suitable as filler and carrier agents. Optionally, these chewable tablet formulations may contain up to about 100 mg of a pharmaceutically acceptable glidants or lubricants. An example of such a chewable tablet is provided below:

| Ingredients | Tablet | Input For 1000 Tablets |
| --- | --- | --- |
| Etodolac Eutomer | 200 mg | 0.200 kg |
| Citric Acid, USP | | 0.020 kg |
| Manitol, USP | | 0.532 kg |
| Polyethylene Glycol, 8000, NF, Powdered | | 0.144 kg |
| Flavor-Spearmint, Aromalok, 180235, Fritzsche | | 0.00480 kg |
| Aluminum Stearate, USP | | 0.00580 kg |
| Theoretical Tablet Weight = | 916.6 mg | |

Manufacturing Procedure For Etodolac Eutomer Chew Tablets

Precaution: All operations must be carried out at a relative humidity not exceeding 30% and at a temperature not exceeding 27° C. (80° F.).

Chewable tablets of this formulation may be prepared by first blending the Etodolac Eutomer, Sorbitol, Citric Acid Polyethylene Glycol 9000, and Spearmint Flavor in a blender for about 10 minutes. This is followed by passing this newly formed blend through a mill using a #14 screen, medium speed, knives forward. Then add the Aluminum Stearate to the mixture and blend for about one (1) minute. This blended mixture should then be compressed into tablets of the correct weight using a ⅝" flat, round, beveled edge punch and die set.

The organoleptically acceptable etodolac eutomer formulations of this invention also include effervescing or foaming formulations. These formulations include any pharmaceutical composition which utilizes the etodolac eutomer in an effervescing formulation, particularly those containing an effervescing or foaming combination of an organoleptically acceptable acid, such as a food grade acid, and a carbonate. Pharmaceutically acceptable acids for use in these formulations include, but are not limited to, citric acid, tartaric acid, malic acid, fumaric acid, adipic acid, ascorbic acid, aspartic acid, erythorbic acid, glutamic acid, and succinic acid. Glycine may also be used as part of the acidic component, if desired, but it is most preferred that glycine not comprise the majority of the acidic component. It is most preferred that the acidic component of these effervescent formulations exceed that of the carbonate component to create an effervescent solution with a pH below 7, more preferably below 6.

The carbonates may include any effervescing or foaming carbonate which is pharmaceutically and organoleptically acceptable, including, but not limited to, sodium bicarbonate, potassium carbonate, sodium carbonate, calcium carbonate, ammonium carbonate, magnesium carbonate, and the like. It is understood that the acidic and carbonate components of these formulations may comprise one or more of the acceptable acids or carbonates.

In the broadest sense, the effervescent or foaming formulations of this invention comprise the active etodolac eutomer plus any active amounts of the acid and carbonate components. Preferably, the portions of these three components comprise a) the desired amount of the etodolac eutomer, b) from about 0.1% to about 50% by weight of the acid component and c) from about 0.1% to 50% by weight of the carbonate component.

For instance, a single dose of this drug may comprise a) 10–1,000 mg of etodolac eutomer, b) 0.5–8 g citric acid, or an equivalent amount of one or more of the other acceptable acids described herein, and c) 0.5–8 g of sodium bicarbonate, or an equivalent amount of one or more of the acceptable carbonates described herein. It will be understood by those skilled in the art that the components of these formulations may be varied depending upon the required dosage of the drug, the desired amount of effervescence or foaming to be created, as well as the pH of the liquid into which the formulation will be added.

It is also understood that, in addition to these three components, the effervescent or foaming formulations of this invention may include any additional pharmaceutically and organoleptically acceptable components, including, but not limited to, fillers, flavoring agents, coloring agents, sweetening agents, binders, pharmaceutically acceptable odor enhancing agents, perfumes, etc. These formulations may also include other pharmaceutically active agents, such as analgesics, antihistamines, antacids, anti-gas agents, etc. Examples of effervescent or foaming formulations within the scope of this invention include the following:

Effervescing Powders Containing the Etodolac Eutomer

One hundred dose batches of an effervescing or foaming powder of this invention can be made by mixing together any of the following combinations, with or without additional components:

EXAMPLE 4 a) 1,000 to 100,000 mg etodolac eutomer
b) 110 g tartaric acid
c) 100 g sodium bicarbonate

EXAMPLE 5 a) 1,000 to 100,000 mg etodolac eutomer
b) 150 g malic acid
c) 150 g fumaric acid
d) 100 grams calcium carbonate e) 180 grams magnesium carbonate e) 100 g fructose

EXAMPLE 6 a) 1,000 to 100,000 mg etodolac eutomer b) 250 g citric acid c) 125 g potassium carbonate d) 100 g ammonium carbonate

EXAMPLE 7 a) 1,000 to 100,000 mg etodolac eutomer b) 10 g citric acid c) 10 g sodium bicarbonate d) 40 g sucrose e) 10 g sorbitol f) 10 g mannitol g) 10 g hydroxypropyl cellulose h) 5 g carboxymethyl cellulose

EXAMPLE 8

Effervescent Tablets Containing the Etodolac Eutomer

To make five hundred 200 mg effervescent tablets:

| Item | Ingredient | Amount | Per Tablet |
|---|---|---|---|
| 1 | Etodolac eutomer, micronized | 100 g | 200 mg |
| 2 | Sodium Bicarbonate | 386 g | |
| 3 | Tartaric Acid | 164 g | |
| 4 | Citric Acid | 250 g | |
| 5 | Polyethylene Glycol 6000 | 100 g | |
| | Theoretical Tablet Weight | 2.0 G | |

Manufacturing Procedure

Precautions: After Step #1 all processes to be accomplished in an environment which does not exceed 30% relative humidity and 27° C.

1. Dry Items 1, 2, 3, and 4 at from 80° C. to 105° C. for from 1 hour to 4 hours.

2. Blend Items 1, 2, 3 and 4 to make a homogeneous powder.

3. Pass the blend from Step #2 through a 60 mesh sieve.

4. Pass Item #5, through a 60 mesh sieve.

5. Add the screened Item #5 to the blend from Step #3 and blend to only just distribute.

6. Compress using a flat, beveled edge, 5/8", punch and die to a 2.0 g tablet weight.

Directions for Use

Place the desired dose, 200 mg per tablet, into a liquid, such as about three fluid ounces of water, and wait for the tablet to completely disintegrate.

EXAMPLE 9

Effervescent Granules with the Etodolac Eutomer

To make 500 sachets or packets of effervescent granules, use the ingredients of Example No. 8 replacing Item No. 5 with dry orange flavor powder (from Virginia Dare, Brooklyn, N.Y. 11232) and replacing Step No. 6 of Example 8 with the following two steps:

Step No. 6: Place the powder obtained from procedure Step No. 5 in a fluidized bed tower and when the powder is suspended with air, add enough water mist to create granules approaching 10 mesh in size.

Step No. 7: Add heat to dry the granules and remove to a not greater than 25% relative humidity area to package in hermetic packets at 2.0 g each.

These effervescent granules may be orally administered after merely adding the desired number of packets of granules to water and waiting until all granules disintegrate.

Rapidly Disintegrating Solid Dosage Forms

Another form in which the organoleptically acceptable compositions of this invention may take are the rapidly dissolving or disintegrating dosage formulations, such as those described in U.S. Pat. No. 4,371,516, the disclosure of which is incorporated herein by reference. These dosing forms are preferably soluble solid forms which are designed to break down in a matter of seconds upon contact with liquids, such as water or the saliva of the recipients mouth. These formulations preferably disintegrate within 10 seconds of contact with liquids. Such formulations are especially useful for administering medicines to pediatric or geriatric patients or others who may not be receptive to the treatment and who may attempt to spit out the medicine or hide a non-disintegrating form in their mouth until it can be thrown away later.

While the process for making rapidly disintegrating dosage forms which are useful with this invention are described in detail in U.S. Pat. Nos. 4,371,516 (Gregory et al.) and 4,305,502 (Gregory et al.), the following examples demonstrate the production of rapidly disintegrating dosage forms containing preferred dosage ranges of the etodolac eutomer.

EXAMPLE 10

75 individual 50 mg rapidly disintegrating doses of the etodolac eutomer can be prepared in the following manner:

a) A hydrolyzed gelatin solution is prepared by dissolving 30.0 grams of gelatin B.P. in 1,000 ml of purified water with the aid of heat and constant stirring. The resulting gelatin solution is then autoclaved at 121° C. and 15 p.s.i. for one hour. The gelatin solution is then allowed to cool to room temperature.

b) An aluminum mold containing 75 cylindrical depressions, each depression being about 0.5 cm in diameter and 1 cm deep, is cooled to about −192° C. in liquid nitrogen contained in a stainless steel tray. 100 g of the etodolac eutomer, 20 g of benzoic acid, 0.25 g of F.D.C. Yellow No. 5 Coloring Agent, and 0.5 g of Norda spray dried orange flavor are mixed with the gelatin solution and mixed continually while ½ ml of the mixture is added to each depression by a hypodermic syringe. The contents of the depressions are allowed to freeze. Then the filled mold is placed in a freeze dryer and processed under a vacuum and controlled heat. The freeze dried formulations, each containing 50 mg of the etodolac eutomer, are then removed from the mold and stored or packaged under controlled humidity conditions. Each formulation will dissolve in a matter of a few seconds when taken orally or added to a liquid.

It will be understood by those skilled in the art that the techniques described above can be used to formulate rapidly disintegrating dosage forms of this invention containing a variety of individual dosages of etodolac eutomer. These solutions may also include a variety of flavoring agents, sweetening agents, coloring agents, etc. to make the solutions more appealing to various recipients. In addition, other carrier materials may be used in exchange for the partially hydrolyzed gelatin. These include, but are not limited to, polysaccharides, such as hydrolyzed dextran, alginates (e.g. sodium alginate), and dextrin, or mixtures thereof with each other or with other carrier materials, including acacia, polyvinyl alcohol or polyvinylpyrrolidine.

For the production of these rapidly disintegrating formulations, it is preferred that the etodolac eutomer utilized be in the form of a micronized powder to eliminate the potential for the perception of a gritty texture as the formulation disintegrates in the recipient's mouth. Most preferably, the etodolac eutomer is in the form of a micronized powder comprising particles of 50 microns or less. It will be understood by those skilled in the art that these formulations, by the nature of their design, will disintegrate if subjected to moisture or physical handling or concussion. Therefore, it is understood that these formulations should be handled with care and packaged in containers which minimize the risk of their premature disintegration, such as the packaging described in U.S. Pat. No. 4,305,502.

The following examples 11 through 14 list combinations of etodolac eutomer and other components which may be added to 1,000 ml of the gelatin solution, or other appropriate carrier materials, in the manner described above.

EXAMPLE 11
10 mg etodolac eutomer/dose
 a) 20 g etodolac eutomer
 b) 30 g fructose
 c) 10 g benzoic acid

EXAMPLE 12
100 mg etodolac eutomer/dose
 a) 200 g etodolac eutomer
 b) 0.25 g F.D.C. Yellow No. 5 Coloring Agent
 c) 0.5 g Norda spray dried orange flavor
 d) 25 g sucrose
 e) 20 g benzoic acid

EXAMPLE 13
200 mg etodolac eutomer/dose
 a) 400 g etodolac eutomer
 b) 0.25 g F.D.C. Yellow No. 5 Coloring Agent
 c) 10 g fructose
 d) 15 g sucrose
 e) 40 g benzoic acid

EXAMPLE 14
400 mg etodolac eutomer/dose—without hydrolyzed gelatin
 a) 533.33 g etodolac eutomer
 b) 17 g sodium alginate
 c) 35 g Dextran
 d) 15 g aspartame
 e) distilled water to 1000 ml
 f) 50 g benzoic acid This formulation of Example 14, not containing the hydrolyzed gelatin of the previous examples, may be produced in depressions on a 220×330 mm plastic, such as polyvinyl chloride (p.v.c.), sheet containing 150 cylindrical depressions, each depression being about 0.7 cm deep and about 1.4 cm in diameter, which has been cooled with solid carbon dioxide. The formulation may be produced by suspending the etodolac eutomer in the water containing the sodium alginate, Dextran and aspartame listed above with the use of ultrasonic vibrations. 0.75 ml of the suspension can then be placed into each of the p.v.c. sheet's depressions, where they can be freeze dried to complete the rapidly disintegrating solid formulation.

EXAMPLE 15
1 g etodolac eutomer/dose—without hydrolyzed gelatin
 a) 1,333.33 g etodolac eutomer
 b) 20 g polyvinylalcohol
 c) 20 g polyvinylpyrrolidine
 d) 30 g sucrose
 e) 0.2 g Tween 80
 f) distilled water—qs to 1000 ml
 g) 50 g benzoic acid Another example of a rapidly disintegrating solid formulation may be produced with the components listed above and the carbon dioxide cooled p.v.c. sheet described in the previous example. This may be done by adding the polyvinylalcohol to about 500 ml of hot distilled water, which is then allowed to cool. The polyvinylpyrrolidine, sucrose and Tween 80 can then be added and the mixture shaken to dissolve all of the solids. The etodolac eutomer is added and dispersed with ultrasonic vibration. This mixture should then be brought to the final volume of 1000 ml by the addition of distilled water. 0.75 ml of this solution may then be added to each depression for freeze drying to the final solid formulation.

Buccal Formulations

Buccal formulation containing the etodolac eutomer of this invention may be produced by the steps and pharmaceutical components set forth in U.S. Pat. No. 4,764,378 (Keith et al.), the contents of which are incorporated herein by reference. It is most preferred that these buccal formulations have incorporated therein an acidic component, such as a micronized solid food acid. Such a food acid may comprise from about 0.1–2.0% of the weight of the final buccal formulation, though more acid may be added if desired.

EXAMPLE 16
Lozenge or Troche Formulations

Lozenge or troche formulations, which may also be referred to as pastilles, containing the etodolac eutomer may also be prepared for any dosage described herein by methods known in the art. For instance, such lozenges may be prepared by molding and subsequently drying by evaporation a concentrated syrup containing the etodolac eutomer, with thickening agents such as acacia or tragacanth gums added, if necessary. This type of lozenge is often referred to as a candy mass lozenge or troche. Using the following ingredients and technique, candy mass lozenges can be made for any dosage of etodolac eutomer described herein. Described below is a formulation useful for producing lozenges containing 100 mg of etodolac eutomer.

| Ingredient | Amount |
| --- | --- |
| Sucrose | 6,000 g |
| Cream of Tartar | 30.0 g (optional) |
| Corn Syrup | 4,000 g |
| Citric Acid (fine powder through 100 mesh) | 100 mg/4 g |
| Etodolac Eutomer | 100 mg/4 g |

These lozenges can be produced by adding the sucrose, cream of tartar (optional) and corn syrup listed above to a stock pot with mixing, followed by boiling to dissolve the sucrose and cream of tartar. These components should be removed from the heat when a stiff boil is achieved, which will occur at about 290° F., and about 30% of the original volume is lost to evaporation. These components should be mixed until the mass cools to approximately 280° F. At this point the citric acid and etodolac eutomer should be added to the mass with mixing to create a homogenous dispersion. When the batch cools to about 190° F. the mass can be rolled into a rope or columnar shape and cut into 4 g pieces. These pieces may then be placed on a mesh to cool to ambient temperatures.

A more readily disintegrating lozenge or troche form may be made using 9200 g of compressible sugar, such as Dipac® brand compressible sugar (Domino Sugar Co., New York, N.Y.), and the amounts of cream of tartar (optional), citric acid and etodolac eutomer (or other preferred dose of the etodolac eutomer) described above. These components may be homogeneously mixed and compressed into lozenges of the desired size, such as the 4 g size described above.

In lieu of compressible sugar, an equivalent amount of sucrose or lactose may be thoroughly mixed with a suitable binding agent, such as about 525 g of sodium alginate, and a pharmaceutically suitable granulating fluid to create a wet mass. This wet mass may be passed through a granulating mill and compressed into lozenges of the desired size.

Dentifrice Compositions

Dentifrice compositions known in the art may have S(+) etodolac, preferably with an additional acidic component, incorporated therein for use in the prevention or reduction of bone loss and/or for promoting regrowth of bone previously lost. It will be understood that dentifrices herein are intended to include any dental formulations that may be used in the treatment and maintenance of teeth and mouth tissues. These include, but are not limited to pastes, gels, powders, granular compositions, liquids, etc. An example of a toothpaste within the scope of this invention can be produced by slowly adding the non-aqueous components listed below to water, followed by conventional mixing with a roller mill.

EXAMPLE 17

| Component | % Composition |
| --- | --- |
| S(+) Etodolac | 1% |
| Magnesium Aluminum Silicate | 1% |
| Citric Acid | 1% |
| Dicalcium Phosphate | 46% |
| Mint or other flavor | |
| Sodium carboxymethylcellulose | 0.5% |
| Sodium Lauryl Sulfate | 2% |
| Water | 44.5% |

The organoleptically acceptable dentifrices within the scope of this invention may include any of the known dentifrice formulations, preferably with an existing or added acidic component. Paste formulations of this type may contain, for example, by weight from 10–50% of an abrasive system, 0.5–10% thickeners, 10–80% humectant, 0.1–1% sweetener, 0.05–2% flavoring agents, 0.001–0.02% coloring agents, 1–7.5% surfactant, 0.1–0.8% antimicrobial preservatives, and 0.01–5% acidifiers.

Abrasive components of these formulations can include calcium pyrophosphate, hydrated silica, insoluble sodium metaphosphate, organic polymers, alumina trihydrate, dicalcium phosphate dihydrate, dicalcium phosphate anhydrous and calcium carbonate. Thickeners can include silica aerogel, pyrogenic silica, silica precipitates, carboxymethylcellulose, carboxy vinyl polymers, xanthan gum and carrageenan. Humectants of use include sorbitols, glycerine and polyethylene glycols. Useful sweeteners include saccharin, xylitol, cyclamate, aspartame and thaumatin. Flavoring agents can be modified according to taste and market acceptability, but include peppermint, spearmint, wintergreen, cinnamon, and anise flavors, as well as essential oils. Any FDA approved coloring agents may be chosen for incorporation into such dental formulations. Surfactants may include sodium laurylsulfate, sodium laurylsarcosinate, pluronics, tweens, sodium cocomonoglyceride sulfonate, sodium dodecylbenzene sulfonate, and dioctylsodium sulfosuccinate. Antimicrobial agents and preservatives for use in this art include parahydroxybenzoates, sorbic acid and benzoic acid. Acid components for these forms include the food acids described herein, including lactic acid, citric acid, phosphoric acid and tartaric acid.

An example of such a dentifrice can be formed from the following ingredients.

EXAMPLE 18

| Ingredient | Function | Weight Percentage |
| --- | --- | --- |
| Etodolac Eutomer | Active Ingredient | 2.0% |
| Silica xerogel | Abrasive | 14.0% |
| Silica aerogel | Thickener | 7.5% |
| Sodium Carboxymethylcellulose | Thickener | 1.0% |
| Sorbitol | Humectant | 60% |
| Saccharin | Sweetener | 0.2% |
| Sodium monofluorophosphate | Fluoride Source | 0.76% |
| Sodium lauryl sulfate (29% Solution) | Surfactant | 5% |
| Tutti Fruitti Flavor (Virginia Dare, AK 27) | Flavoring Agent | 1% |
| Equal Parts Ethylparaben, Methylparaben and Propylparaben | Antimicrobial Preservatives | 0.4% |
| FDC Blue No. 1 | Coloring Agent | 1% |
| Phosphoric Acid | Acidifier | q.s. to pH 5.0–5.2 |
| Water, demineralized | Vehicle | q.s. to 100% |

To minimize any possibility of demineralization of tooth structure, it is suggested that the pH of this formulation not be lower than about 5.0. Sodium monofluorophosphate is an appropriate fluoride source for use within this desired pH range.

Chewing Gum Formulations

Another organoleptically acceptable formulation within the scope of this invention are chewing gum types of formulations. It will be understood that these types of formulations can be created by incorporating the etodolac eutomer, most preferably along with a suitable acidic component, into any of the organoleptically acceptable chewing gum bases. An example of a chewing gum formulation of this invention can be made with the components seen below in Example 19.

EXAMPLE 19

| Ingredient | Function in Formulation | Amt. per 3 g Unit | Amt. per 3 kg batch |
| --- | --- | --- | --- |
| Etodolac Eutomer, micronized | Active Ingredient | 0.010 g | 10 g |
| Chicle | Gum Base | 1.000 g | 1000 g |
| Glycerol ester of hydrogenated rosin | Gum Base | 0.200 g | 200 g |
| Sucrose, fine powder | Sweetener | 1.600 g | 1600 g |
| Balsam Tolu | Acidifier | 0.187 g | 187 g |
| Cinnamon Oil | Flavoring Agent | 0.003 g | 3 g |

The components listed above can be combined into a chewing gum formulation by warming the gum base ingredients to a softened stage, followed by separate addition steps for the acidifier, sweetener, etodolac eutomer and flavoring agent, with kneading to produce a homogenous mixture following each addition. The final homogenous chewing gum formulation can then be rolled out with a sizing machine and cut into 3 g pieces using finely powdered sucrose to facilitate handling, followed by standard wrapping and packaging. It is understood that other chewing gum formulations may be utilized within the scope of this invention and that the components of the formulation described above may be replaced with equivalent amounts of other functional components, including those described herein for use with other formulations.

Veterinary Formulations

It is also understood that the use of organoleptically acceptable formulations is important in veterinary applications. While this is true for any mammal which a veterinary specialist may recommend the use of an NSAID, it is particularly true in the case of companion animals, such as dogs and cats, where owners and handlers appreciate the relative ease of administering readily accepted oral dosage formulations, as opposed to those which must be administered with animal restraint techniques.

Veterinary formulations of this invention include any of the solid or liquid dosage forms mentioned above which may also be given to animals. These formulations may be incorporated into an animal's food or drink or given as a separate pharmaceutical entity. If given separately, it is recommended that the formulation contain an ingredient, preferably a taste ingredient, which is normally found appealing to the animal in question. For example, with cats and dogs a flavor base component of liver digest, seafood digest, poultry digest, desiccated liver, soya flour, sugar, cod liver oil, soy bean meal, fish meal, bone meal, yeast, wheat germ meal, fish meal or other known food bases or a combination thereof may be used. Such ingredients may be used as flavoring agents in the formulations listed above or they may be used as fillers in place of other materials described herein. It will be understood that the percentages of ingredients in animal-oriented oral formulations of this invention will be determined in large part by the size of the animal and the size of the desired formulation. For instance, a relatively small chewable tablet may consist of a mixed and compressed combination of the following:

EXAMPLE 20

| Ingredient | Weight Percentage |
|---|---|
| Etodolac Eutomer | 60% |
| Flavor Base Component | 15–25% |
| Microcrystalline Cellulose | 10–20% |
| Povidone K29-32 | 2–6% |
| Aluminum Stearate | 1–2% |
| Lactic Acid | 0.1–2.0% |

To create a larger solid formulation containing a desirable dosage of the etodolac eutomer, the amounts of the components may be increased as desired, such as with the following formulation:

EXAMPLE 21

| Ingredient | Weight Percentage |
|---|---|
| Etodolac Eutomer | 15% |
| Flavor Base Component | 35–45% |
| Dibasic Calcium Phosphate | 15–25% |
| Microcrystalline Cellulose | 15–25% |
| Povidone K29-32 | 2–6% |
| Aluminum Stearate | 1–2% |

It would be most preferred that these formulations also contain an acidic component, such as a solid food acid. For instance, a food acid such as citric or malic acid can comprise from 1–5% of the weight of the formulation, though the amount of acidic component may be raised if desired. Another chewable solid formulation which may be useful for animal administration would be the following:

EXAMPLE 22

| Ingredient | mg/tablet |
|---|---|
| Etodolac Eutomer | 5–500 |
| Whey, Dry Sweet | 2,000 |
| Liver, Desiccated | 210 |
| Yeast, Dried | 50 |
| Aluminum Stearate, NF | 50 |
| Citric Acid | 30 |

EXAMPLE 23

Another chewable tablet formulation for use with companion animals can be produced with the following components and methods. While this example shows the production of 200 mg tablets containing the etodolac eutomer, it will be understood that any dosage required can be formulated in this type of formulation.

| Ingredients | Amount/Tablet | Amount/1,000 Tablet Batch |
|---|---|---|
| Etodolac Eutomer | 200 mg | 200 g |
| Sodium Starch Gycolate, NF (SSG) | 600 mg | 600 g |
| Spray Dried U.S.P. Lactose | 4441 mg | 441 g |
| Desiccated Liver | 252 mg | 252 g |
| Dried Yeast | 62 mg | 62 g |
| Aluminum Stearate | 45 mg | 45 g |
| Fumaric Acid | 100 mg | 100 g |

Chewable tablets of this formulation can be produced by blending the etodolac eutomer, sodium starch glycolate, spray dried lactose, fumaric acid, desiccated liver and dried yeast in a suitable mixer until uniform. Then ⅔ of the quantity of aluminum stearate can be added to a portion, such as approximately 10%, of the mixture of ingredients just described with mixing until uniform. The remaining mass of the ingredients can then be added with sufficient mixing to distribute the aluminum stearate-containing mass. This blended mixture may then be slugged medium hard and sized through a rotary granulator using a #10 screen. The remainder of aluminum stearate can then be added to the granulated mixture with mixing. The final tablets of this formulation can be compressed into tablet form, such as by using a 1¹⁄₁₆" flat face punch at a hardness of from 12 to 15 SCU. Tablets of this type may be either given whole or broken into smaller sections for lower dosage deliver.

EXAMPLE 24

Equilibrium solubility data for S(+)-etodolac based on pH was determined by placing excess amounts of the S(+)-etodolac and about 5 mL of the dissolution medium in screw-capped vials which were covered with aluminum foil and then tumbled in a 25° C. water bath for 3 days. Slurries were filtered through $\mu$m pore-size Gelman disposable filters. Filtrates were appropriately diluted with their dissolution medium and analyzed by a Cary 210 UV-VIS spectrophotometer at 278 nm.

The dissolution media used for the pH-solubility profile and ionic strength effect were HCl, HAc—NaAc, $KH_2PO_4$—NaOH, $K_2CO_3$—$KHCO_3$, $H_3BO_3$—NaOH, and NaOH solutions, where the ionic strengths of media were adjusted to be 0.1 by the addition of NaCl. Those solvent systems used for cosolvent solubilization were various ratios of PEG 400, ethanol, triethanolamine (TEA), and dimethylacetamide (DMA) to aqueous solutions. pH values of the slurries were measured before and after equilibrium.

Solubility (mg/mL) of (+)-etodolac as a Function of pH at 25° C.

| # | Dissolution Medium | pH before Equilibrium | pH after Equilibrium | Solubility (mg/mL) |
|---|---|---|---|---|
| 1 | 0.1 N HCl | 1.10 | 1.14 | 0.080 |
| 2 | 0.1 N HCl | 2.07 | 2.13 | 0.080 |
| 3 | 0.001 N HCl | 3.05 | 3.24 | 0.073 |
| 4 | 0.1 M Acetate Buffer | 4.00 | 4.03 | 0.093 |
| 5 | 0.1 M Acetate Buffer | 4.40 | 4.41 | 0.120 |
| 6 | 0.1 M Phosphate Buffer | 4.62 | 4.63 | 0.193 |
| 7 | 0.1 M Phosphate Buffer | 4.99 | 4.98 | 0.263 |
| 8 | 0.1 M Phosphate Buffer | 6.00 | 5.82 | 1.212 |
| 9 | 0.01 M Phosphate Buffer | 7.01 | 6.40 | 4.563 |
| 10 | 0.01 M Phosphate Buffer | 8.04 | 6.63 | 7.810 |
| 11 | 0.04 M Borate Buffer | 9.0 | 8.61 | 11.62 |
| 12 | 0.04 M Phosphate Buffer | 10.0 | 8.59 | 15.27 |
| 13 | 0.001 N NaOH | 11.0 | 8.50 | 32.30 |
| 14 | 0.1 N NaOH | 13.0 | 7.15 | 29.40 |
| 15 | 0.2 N NaOH | 13.3 | 7.30 | 58.80 |

*Ionic strength of the dissolution medium was adjusted to be 0.1 by addition of NaCl.

Solubility (mg/mL) of Racemic Etodolac in Various Cosolvent Systems at Room Temperature

| Org (%) | TEA (±)-EA | DMA (±)-EA | EtOH (±)-EA | PEG 400 (±)-EA |
|---|---|---|---|---|
| 2 | 37.74 | — | — | — |
| 4 | 75.93 | — | — | — |
| 6 | 121.60 | — | — | — |
| 8 | 225.66 | — | — | — |
| 10 | 294.18 | 0.468 | — | — |
| 20 | — | 0.956 | 0.279 | 0.905 |
| 30 | — | 2.988 | — | — |
| 40 | — | 7.281 | 2.335 | 3.578 |
| 50 | — | 34.949 | — | — |
| 60 | — | 52.054 | 23.770 | 20.189 |
| 80 | — | 2631 | 101.826 | 152.5 |
| 100 | 101.90 | 4734. | 234.14 | 1733.0 |

Solubility (mg/mL) of S(+)Etodolac in Various Cosolvent Systems at Room Temperature

| Org (%) | TEA (±)-EA | DMA (±)-EA | EtOH (±)-EA | PEG 400 (±)-EA |
|---|---|---|---|---|
| 2 | 39.41 | — | — | — |
| 4 | 77.75 | — | — | — |
| 6 | 126.10 | — | — | — |
| 8 | 234.55 | — | — | — |
| 10 | 295.45 | 0.468 | — | — |
| 20 | — | 1.248 | 0.412 | 0.663 |
| 30 | — | 3.555 | — | — |
| 40 | — | 9.956 | 3.529 | 3.06 |
| 50 | — | 89.055 | — | — |
| 60 | — | 256.34 | 43.669 | 16.256 |
| 80 | — | 419.06 | 126.06 | 642.85 |
| 100 | 81.66 | 757.80 | 283.57 | 3460. |

(±)-EA - racemic etodolac
(±)-EA - (±)-etodolac
TEA - triethanolamine
EtOH- ethanol
PEG 400 - polyethylene glycol Based upon the disclosure herein, those skilled in the art will be able to utilize S(+) etodolac to create a variety of organoleptically acceptable oral formulations within the scope of this invention.

What is claimed:

1. An organoleptically acceptable oral pharmaceutical composition comprising non-solubilized S(+) 1,8-diethyl-1,3,4,9-tetrahydropyrano[3,4-b]indole-1-acetic acid substantially free of R(−) 1,8-diethyl-1,3,4,9-tetrahydropyrano[3,4-b]indole-1-acetic acid and a pharmaceutically and organoleptically acceptable acidic component, the acidic component being of sufficient amount to maintain the pH of the formulation between about 2 and about 6.

2. The organoleptically acceptable oral pharmaceutical composition of claim 1 in which the acidic component is selected from the group consisting of citric acid, tartaric acid, malic acid, fumaric acid, lactic acid, adipic acid, ascorbic acid, aspartic acid, erythorbic acid, glutamic acid, succinic acid, phosphoric acid, hydrochloric acid, and benzoic acid, or mixtures thereof.

3. The organoleptically acceptable oral pharmaceutical composition of claim 1 wherein the acidic component exists in sufficient amount to maintain the formulation at a pH between about 2 and about 5.

4. The organoleptically acceptable pharmaceutical composition of claim 1 further comprising an organoleptically acceptable pharmaceutical carrier.

5. An organoleptically acceptable pharmaceutical composition of claim 1 which comprises a chewing gum formulation.

6. An organoleptically acceptable pharmaceutical composition of claim 1 which is contained within a powdered or granular formulation.

7. An organoleptically acceptable pharmaceutical composition of claim 1 which is contained within a liquid formulation.

8. An organoleptically acceptable pharmaceutical composition of claim 1 which is contained within a chewable tablet formulation.

9. An organoleptically acceptable pharmaceutical composition of claim 1 which is contained within an effervescent formulation.

10. An organoleptically acceptable pharmaceutical composition of claim 1 which is contained within a lozenge formulation.

11. An organoleptically acceptable pharmaceutical composition of claim 1 which is contained within a rapidly disintegrating solid dosage formulation.

12. An organoleptically acceptable pharmaceutical composition of claim 1 which comprises a chewable veterinary formulation.

* * * * *